(12) United States Patent
Cheung et al.

(10) Patent No.: US 7,867,372 B2
(45) Date of Patent: Jan. 11, 2011

(54) APPARATUS AND METHOD FOR PERFORMING VERTICAL ELECTROPHORESIS

(75) Inventors: To Cheung, Chai Wan (HK); Long Yin Zhu, Beijing (CN); Yan Li, Beijing (CN)

(73) Assignee: Baygene Biotech Company Limited, Beijing (CN)

( * ) Notice: Subject to any disclaimer, the term of this patent is extended or adjusted under 35 U.S.C. 154(b) by 375 days.

(21) Appl. No.: 12/065,608

(22) PCT Filed: Sep. 28, 2006

(86) PCT No.: PCT/IB2006/053531

§ 371 (c)(1),
(2), (4) Date: Mar. 4, 2008

(87) PCT Pub. No.: WO2007/036896

PCT Pub. Date: Apr. 5, 2007

(65) Prior Publication Data

US 2008/0202935 A1 Aug. 28, 2008

(30) Foreign Application Priority Data

Sep. 29, 2005 (CN) .................... 2005 2 0122088 U

(51) Int. Cl.
*G01N 27/447* (2006.01)
*G01N 27/26* (2006.01)

(52) U.S. Cl. .................. 204/618; 204/467; 204/616; 204/466

(58) Field of Classification Search ................ 204/616, 204/618, 600–650, 456–467; 422/101
See application file for complete search history.

(56) References Cited

U.S. PATENT DOCUMENTS

| 4,929,329 | A | * | 5/1990 | Danby et al. ................ 204/608 |
| 6,110,340 | A | * | 8/2000 | Lau et al. ..................... 204/467 |
| 6,942,775 | B1 | * | 9/2005 | Fox ............................. 204/467 |
| 2001/0008613 | A1 | * | 7/2001 | Kaltenbach et al. ......... 422/101 |
| 2004/0195103 | A1 | * | 10/2004 | Zhou ........................... 204/467 |

* cited by examiner

*Primary Examiner*—Alexa D Neckel
*Assistant Examiner*—Jennifer Dieterele
(74) *Attorney, Agent, or Firm*—Eagle IP Limited; Jacqueline C. Lui

(57) ABSTRACT

An apparatus for performing vertical electrophoresis comprises a main body, a pair of gel plates, a pair of clamping devices, and a lower buffer tank. The clamping devices are slidably attachable to the sides of the main body between a loading position for allowing the gel plates to be inserted into the main body, and a locking position for allowing secure attachment of the gel plates to the main body by a single horizontal sliding movement.

14 Claims, 11 Drawing Sheets

APPARATUS AND METHOD FOR PERFORMING VERTICAL ELECTROPHORESIS

RELATED APPLICATIONS

This patent application is a National Stage of International Application Ser. No. PCT/IB2006/053531, filed on 28 Sept. 2006, which claims the benefit of a Chinese Patent Application Ser. No. 200520122088.0, filed on 29 Sept. 2005, the disclosures of which are all incorporated herein by reference in their entireties.

FIELD OF INVENTION

This invention relates to an apparatus and method for performing vertical electrophoresis.

BACKGROUND OF INVENTION

Gel electrophoresis is a commonly used and well-known technique for segregating mixtures. A gel matrix is used as a medium for the molecules to move therethrough at different rates based on their characteristics when an electric current is applied to the gel. Its usage is mainly found in the biotechnology area such as DNA sequencing or cloning.

Gel tanks for performing electrophoresis are available from different commercial manufacturers, with models dedicated to gel being held in a vertical position are popular among users. Numerous designs are available to attach the gel plates to the main body of the apparatus that are convenient and leak-proof.

SUMMARY OF INVENTION

It is an object of the present invention to provide an alternative design for an apparatus for performing vertical gel electrophoresis.

Accordingly, the present invention, in one aspect, is an apparatus for performing vertical gel electrophoresis comprising a main body, at least one pair of gel plates, at least one pair of clamping devices, and a lower buffer tank. The clamping devices are attachable to the main body and used for securing the attachment of the gel plates to the main body in a position that an upper buffer tank is formed. The lower buffer tank connects with the main body and the gel plates such that a gel cast within the gel plates acts to electrically connect the upper and lower buffer tanks during operation. The slidable attachment of the clamping devices to the main body allows for horizontal sliding movement of the clamping devices between a loading position and a locking position. When the clamping devices are in the loading position, gel plates are allowed to insert into the main body, whereas when the clamping devices are transferred into the locking position, a secure attachment of the gel plates to the main body is obtained.

In a preferred embodiment of the present invention, the main body contains a pair of H-shaped frames with each frame further containing two side panels and a bridge disposed therebetween. Each clamping device is U-shaped and contains a first ledge, a second ledge connected to and facing the first ledge, and a bolstering panel coupled to the interior side of the first ledge with a fixing mechanism for fixedly mounting the gel plates to the main body. In addition, the side panel further comprises an inner abutment panel and an outer abutment panel extending therefrom, with the two abutment panels being positioned in a manner that a channel is formed therebetween. The channel is used for accommodating the second ledge of the clamping device into the locking position such that the clamping device may be conveniently slid between the loading and locking positions. The main body further contains an upper board and lower board connecting to the top and the bottom of each side panel of the H-shaped frames respectively.

In a more preferred embodiment, the clamping device further contains at least a pair of grooves provided within each end of the first ledge. Each upper and lower board is made up of at least a rail extending horizontally thereacross and protruding towards the center of the main body. Each rail is used for coupling with the groove of the corresponding clamping device to guide the horizontal sliding movement of the clamping device between the loading and locking positions.

In another preferred embodiment, the clamping device comprises at least a rail provided on each end of the first ledge and extending thereacross. Each upper and lower board contains at least a pair of grooves provided therewithin. Each rail protrudes towards the center of the camping device for coupling with the grooves disposed within the corresponding upper or lower board to guide the horizontal sliding movement of the clamping device between the loading and locking positions.

In another implementation, the main body further comprises a base panel adjoining the two bridges of the two H-shaped frames such that a partial upper buffer tank is formed from the space created therebetween, with the base panel acting as the floor of the partial upper buffer tank. The apparatus further contains an inverted V-shaped open conduit extending horizontally across and below the base panel, with each end of the conduit connecting to each side panel above a side hole provided on the side panel. Consequently, during operation, bubbles formed in the lower buffer tank are diverged along the conduit to the sides of the main body through the side holes.

In yet another implementation, the gel plates contain an inner plate fixed and juxtaposing an outer plate to create a gel space therebetween. In a more preferred embodiment, the gel plates are made of ceramic. Each H-shaped frame is further made of a gasket of uniform thickness and a gasket of non-uniform thickness. A U-shaped slot is disposed along the two side panels and the bridge of the H-shaped frame and adapted to receive a rubber gasket used for forming a leak-proof seal between the inner plate and the H-shaped frame during operation. The rubber gasket is interchangeable between the gaskets of uniform thickness and non-uniform thickness in which the former gasket is adapted to a notched inner plate containing a pair of lugs projecting from a rectilinear plate, and the latter gasket is adapted to an inner plate without lugs.

There are many advantages to the present invention. For instance, in some designs disclosed in the prior art, the clamps for clamping gel plates are attachable to the main body by rotational movements through a combination of pivot and pin. Consequently, the clamps may need to be rotated into a larger opening angle for swift insertion of gel plates thereto. Also, such rotational motions may make scratches onto the gel plates on transferring the gel plates into and out of the clamps. As described above, the clamping devices of the instant invention are slidably attachable to the main body with limited rotational movements and so the chances for making scratches on the glass plates resulted from the rotations of the clamping devices can be reduced.

According to the instant invention, during operation, any bubbles formed in the lower buffer tank are diverged to the sides of the main body along the inverted V-shaped open conduit. Consequently, fewer bubbles would be accumulated in the front and at the back of the lower buffer tank which would otherwise hinder the observations on the progress of the process.

Another advantage of the present invention is that for a dual gel configuration (where an additional pair of clamping devices is equipped to the main body), the two clamping devices on the same side may be combined into one piece, such that a single lateral push of the clamping device would result in the movement of both clamping devices of the same side. This reduces the effort needed for a user to set up the apparatus such that two pieces of gel can be fixed simultaneously and the efficiency is thus highly enhanced.

DETAILED DESCRIPTION OF THE PREFERRED EMBODIMENTS

Figure 1:
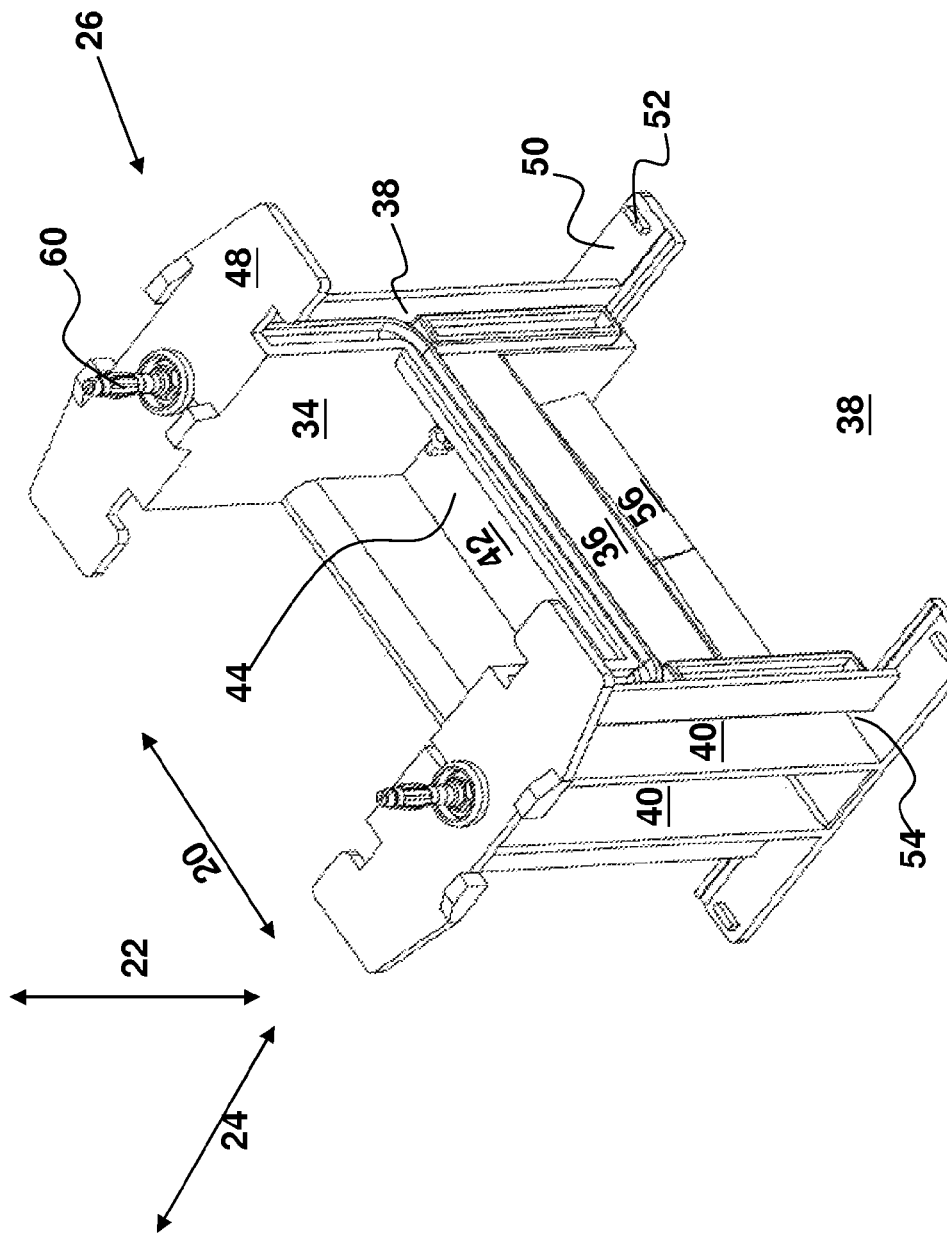
FIG. 1 is a perspective view of a main body without the attached side clamps of an apparatus for performing vertical electrophoresis according to one embodiment of the present invention.

As used herein and in the claims, "comprising" means including the following elements but not excluding others. The "horizontal direction", "vertical direction", and "lateral direction" are as shown in relations to the main body by the arrows 20, 22, and 24 respectively in FIG. 1 for ease of description.

Figure 5:
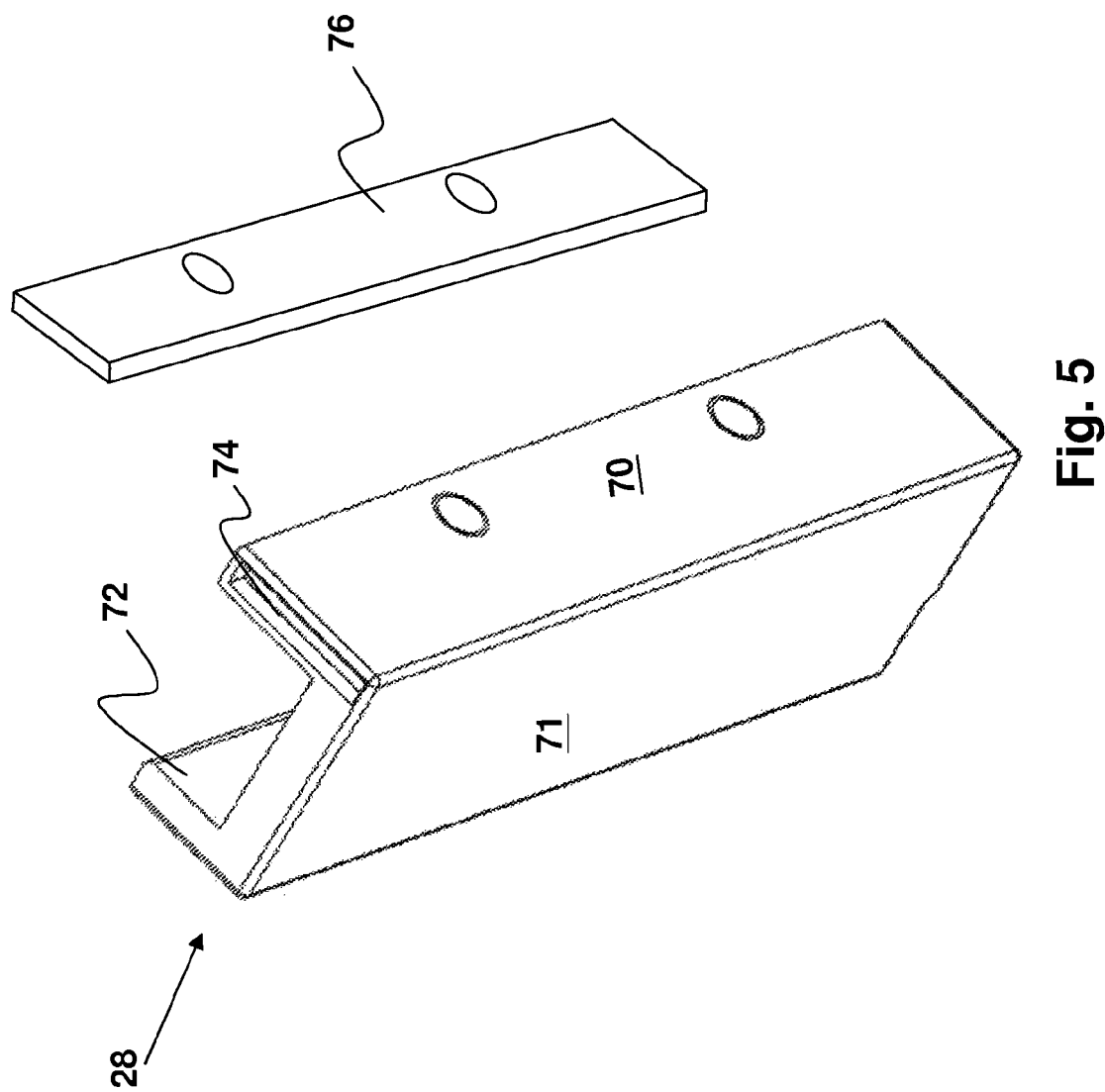
FIG. 5 is a perspective view of a side clamp according to the same embodiment of the present invention.
Figure 6:
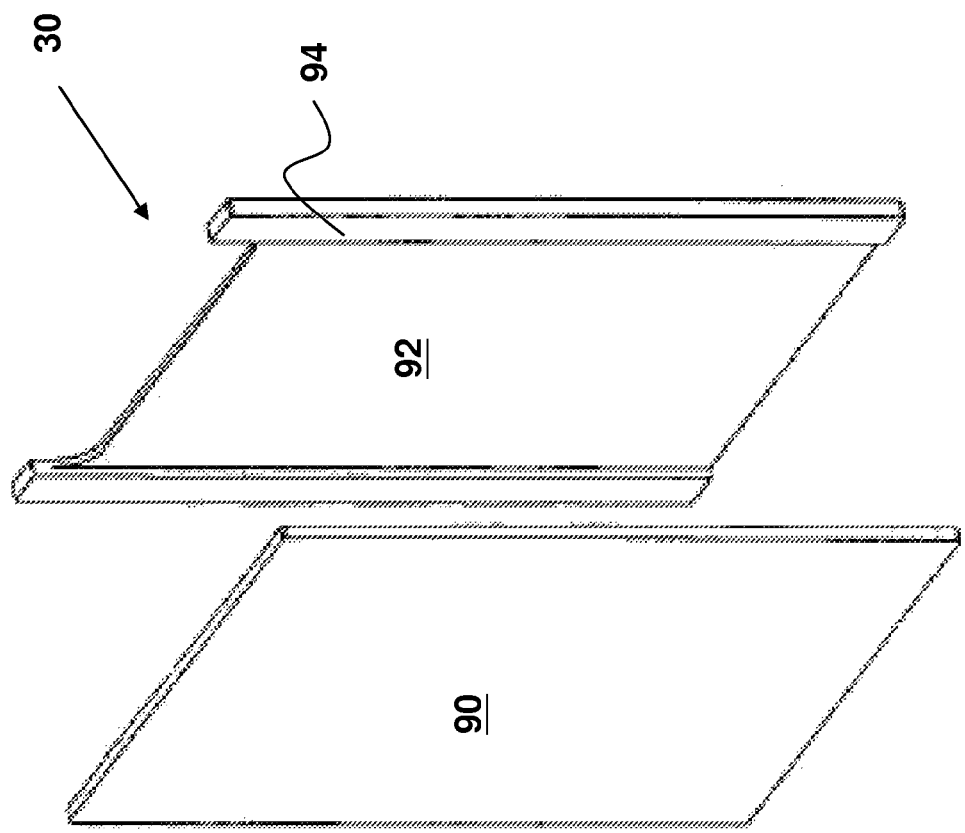
FIG. 6 is a perspective view of a pair of gel plates according to the same embodiment of the present invention.

Referring first to FIGS. 1, 2, 3, and 4, the first embodiment of the present invention is an apparatus for performing vertical electrophoresis comprising a main body 26, two pairs of clamping devices 28 (shown in FIG. 5) and a pair of gel plates 30 (shown in FIG. 6).

Figure 2:
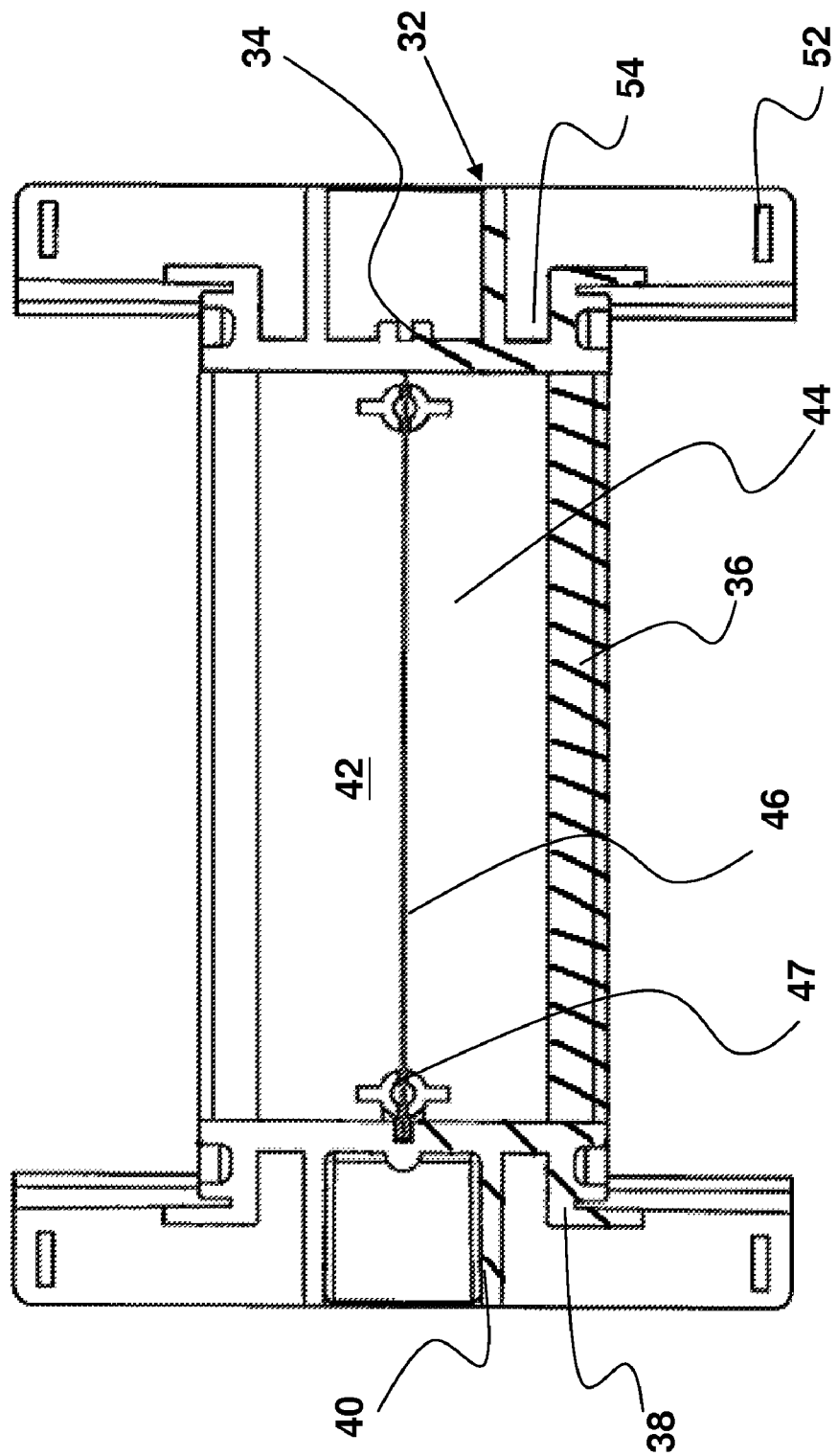
FIG. 2 is a top sectional view of the main body according to the same embodiment of the present invention.
Figure 3:
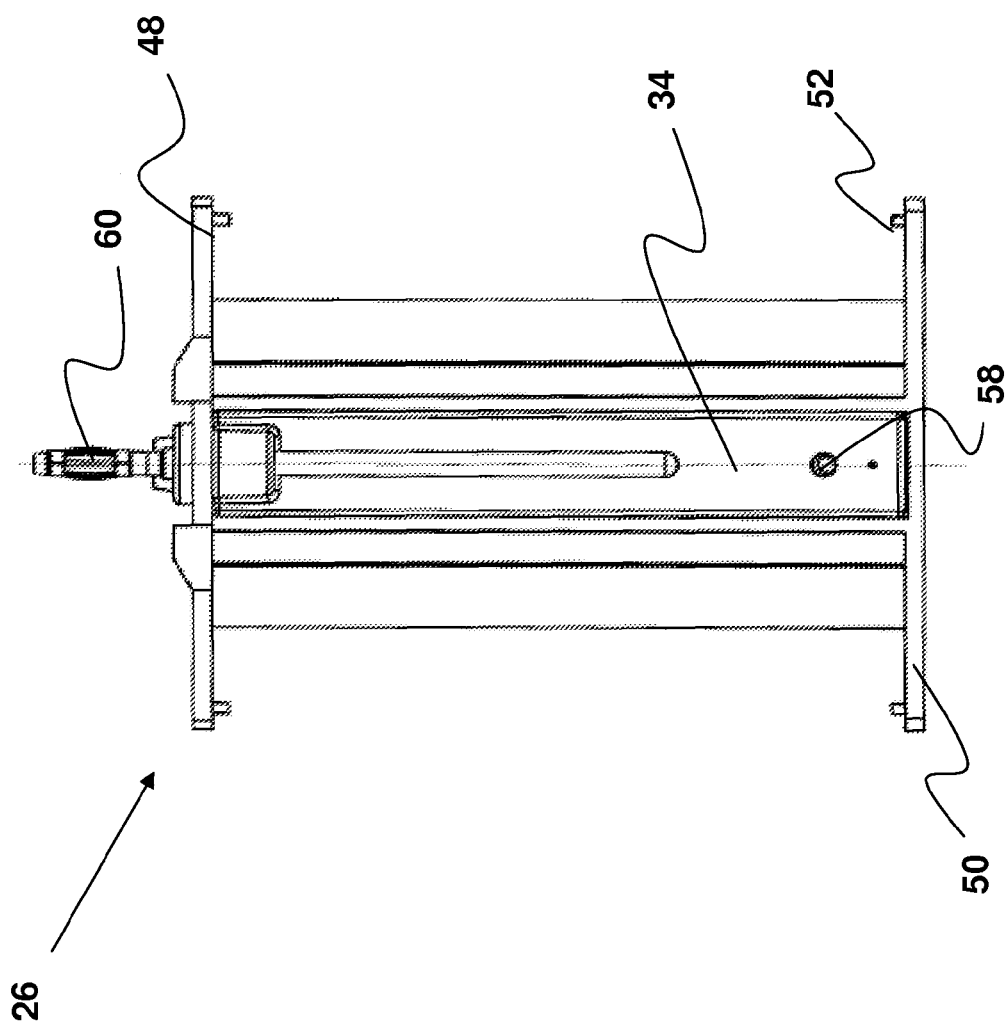
FIG. 3 is a side view of the main body according to the same embodiment of the present invention.

As illustrated in FIG. 2, the main body 26 contains a pair of H-shaped frames 32, with each H-shaped frame 32 further containing two side panels 34 and a bridge 36 therebetween. In this embodiment, the bridge 36 is a vertically disposed panel spanning horizontally with each side panel 34 being a vertical panel attached to the two ends of the bridge 36. On each side panel 34, an outer abutment panel 38 and an inner abutment panel 40 are disposed thereon. The inner abutment panel 40 is a vertical panel with the plane spanning across the horizontal direction and perpendicular to the plane of the side panel 34, whereas the outer abutment panel 38 is an L-shaped vertical panel with the plane of the interior portion extending outwards in parallel with the inner abutment panel 40. The two abutment panels (38 and 40) are positioned in a manner that a channel 54 is created therebetween.

On both sides of the frame 32, the side panels 34 join the two H-shaped frames 32 together and in the embodiment shown forms an integral piece. The two H-shaped frames 32 are further connected by a horizontally disposed base panel 42 attaching to the bottom sides of the two horizontally disposed bridges 36. Consequently, a partial upper buffer tank 44 is defined from the space bounded therebetween with the base panel 42 acting as the floor. A wire 46 is provided inside the partial upper buffer tank 44 and secured on the base panel 42 by the wire fixing nuts 47 disposed thereon.

Figure 4:
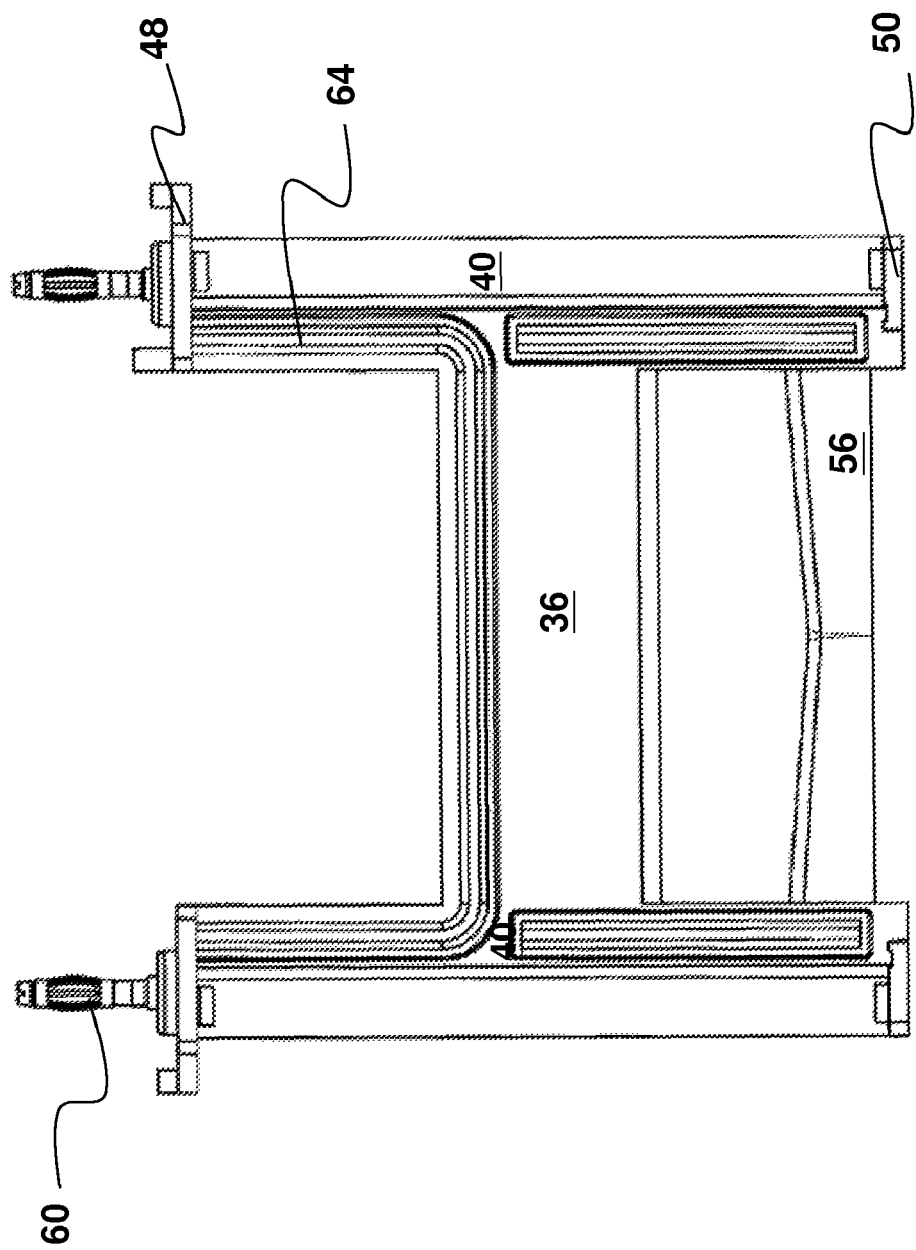
FIG. 4 is a front view of the main body according to the same embodiment of the present invention.

As illustrated in FIG. 4, the main body 26 further comprises an inverted V-shaped open conduit 56 provided below the base panel 42 and horizontally disposed thereacross. The conduit 56 opens towards the bottom of the main body 26 with each end attaching to the integrated side panel on each side of the H-shaped frame 32. A side hole 58 is further disposed on the intersection of the side panels 34 and positioned at the vertex of the "V-shape" of the conduit 56 (in practice, the side panel exists as an integral piece but is described as two pieces in this specification simply for ease of description). A metal wire (not shown) extends along the conduit 56.

Referring back to FIG. 1, an upper board 48 and a lower board 50 are fixed to each side of the H-shaped frame 32 at the top side and the bottom side respectively. The two boards (48 and 50) are horizontally disposed panels with the planes being perpendicular to the plane of the frame 32. A rail 52 extends horizontally across each end of each upper board 48 and lower board 50 and protrudes towards the center of the main body 26. In a more preferred embodiment, the rail 52 is of rectangular shape which in turn limits movement of the clamping devices 28 relative to the main body 26 to substantially a sliding movement, with minimum rotational dislocation. An electrode 60 runs through each upper board 48 with the positive anode connecting to the lower wire and the negative cathode to the upper wire.

Turning now to FIG. 5, the clamping device 28 is elongated and U-shaped in this preferred embodiment and comprises a first ledge 70, a second ledge 72, and a bolstering panel 76 (shown detached from the clamping device 28). Both the first ledge 70 and second ledge 72 extend from the longitudinal length of the clamp and are axially adjoined at one edge to a connecting ledge 71. Since the plane of the connecting ledge 71 is perpendicular to the planes of both ledges (70 and 72), the aforesaid connection creates a U-shaped opening therebetween. The bolstering panel 76 is attached in parallel to the first ledge 70 and adjustably coupled to the first ledge 70 by the connection of fixing screws 78 (shown in FIG. 8) through internally threaded holes disposed thereon. A groove 74 is further disposed within each end of each first ledge 70 and is adapted to mate with the rail 52 on the upper board 48 and lower board 50 when the clamping device 28 is coupled to the main body 26.

Figure 7:
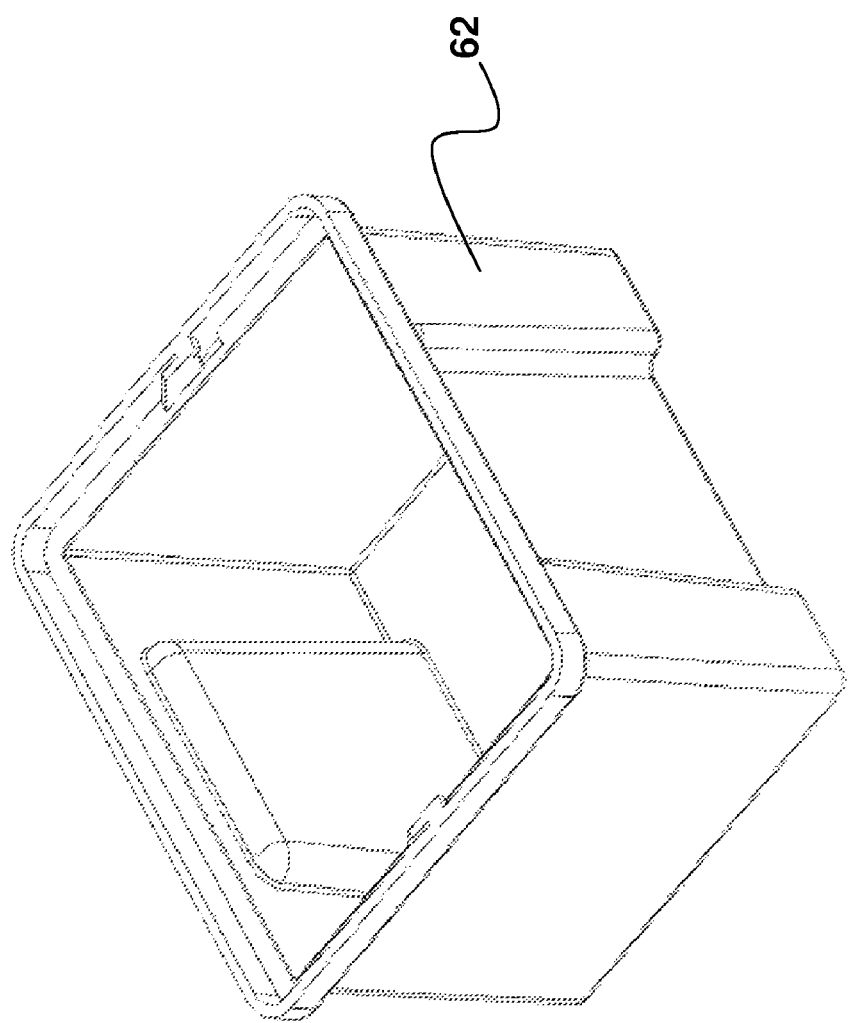
FIG. 7 is a perspective view of a tank according to the same embodiment of the present invention.

As illustrated in FIG. 6, a pair of gel plates 30 contains an outer plate 90 and an inner plate 92. The inner plate 92 is shorter than the outer plate 90 and has two lugs extending from the two edges of the same end of the vertical side. Two separating bars 94 are attached along the two edges of the vertical side on one surface of the inner plate 92 and extend to the ends of the lug extensions. Consequently, when the inner plate 92 is attached to the outer plate 90, a gel space is provided therebetween. A lower buffer tank 62 as shown in FIG. 7 is an open rectangular shaped container.

During operation, a pair of clamping devices 28 is first coupled to the main body 26 by inserting the rails 52 into the grooves 74 at the top and bottom of the first ledge 70 such that the first ledge 70 is interpolated between the upper board 48 and the lower board 50. In this way, the clamping device 28 is now slidable horizontally along the groove 74 between the loading and locking positions. As shown by arrows 80a and 80b of FIG. 8, the clamping device can slide horizontally outwards and extends fully away from the main body to the loading position. This horizontal sliding movement is guided by the traversing of the rail 52 within the groove 74, and the interpolating relationship of the second ledge 72 with the channel 54 (in the direction as shown by arrows 80a and 80b). For clarity of illustration, the clamping device 28 on the right side of FIG. 8 has been completely slid out and detached from the main body 26. In practice, the limit of the loading extension in the loading position is determined by the edge of the groove 74 as it is abutted against the rail 52.

Once a user has moved the clamping devices 28 into the loading position, gel plates 30 (assuming the gel plates have already been cast with a gel using conventional methods before attaching the main body) may be inserted into the main body 26 by a single motion in the lateral direction, with the inner plate 92 being pressed against a rubber gasket (not shown) previously installed onto a U-shaped slot 64 (shown in FIG. 4) disposed along the two side panels 34 and the bridge 36 of the H-shaped frame 32.

Figure 9:
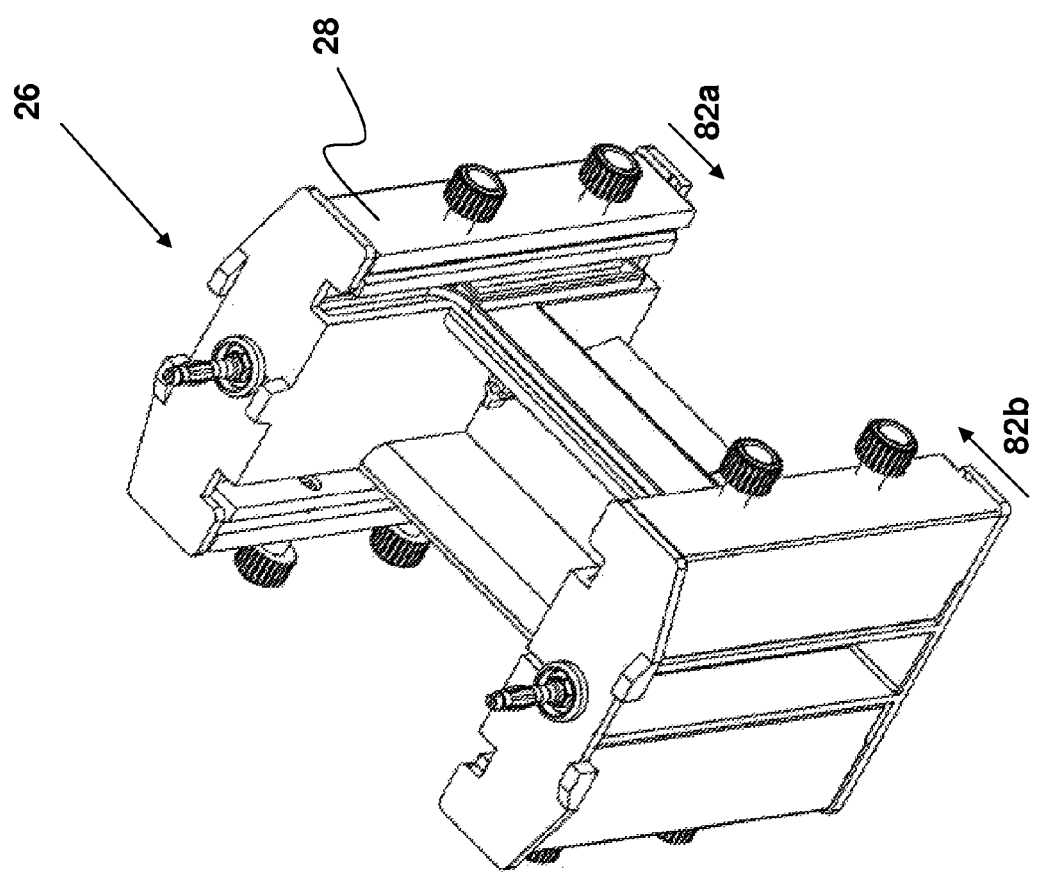
FIG. 9 is a perspective view of a main body with the attached clamps in the locking position according to the same embodiment of the present invention.

Upon attachment of gel plates 30 to the main body 26, the pair of clamping devices 28 may be slid horizontally towards the main body 26 into the locking position as shown in FIG. 9 (without showing the gel plates 30). This horizontal sliding motion is guided by another traverse movement of the rail 52 within the groove 74 and the insertion of the second ledge 72 into the channel 54 (as shown by arrows 82a and 82b). The gel plates 30 are now loosely sandwiched between the H-shaped frame 32 and the bolstering panel 76. The user can then tighten the fixing screws 78 to press the bolstering panel 76 towards the gel plates 30 to secure said attachment.

Figure 8:
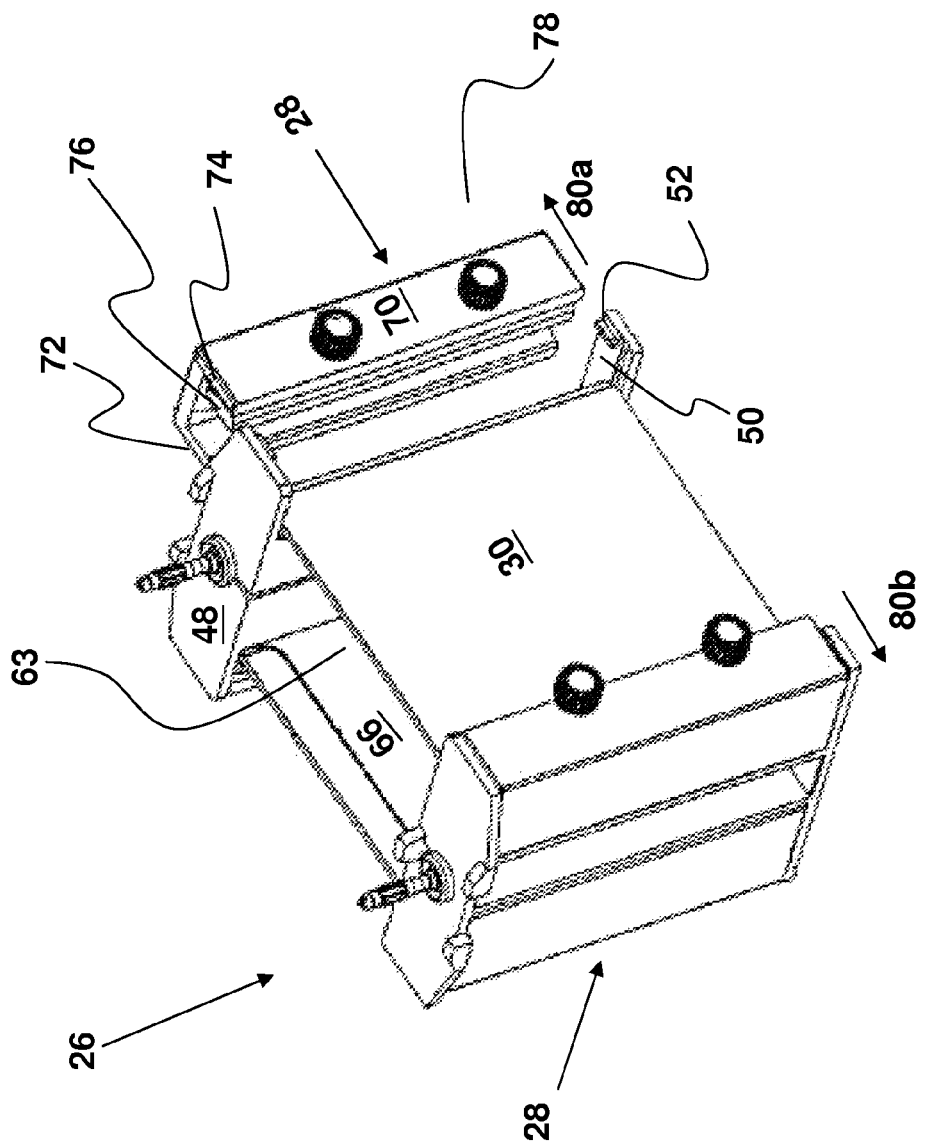
FIG. 8 is a perspective view of a main body with the clamping device on the right side of the figure detached from the main body and the clamping device on the left side of the figure in the locking position according to the same embodiment of the present invention.

In this embodiment, the apparatus is capable for holding one gel onto each of the two H-shaped frames 32 in a single run. Therefore, an additional pair of gel plates 66 may be attached as shown in FIG. 8. An upper buffer tank 63, derived from the partial upper buffer tank 44, is then created when the two pairs of gel plates (30 & 66) attach to the main body 26.

The loaded main body is then inserted into the lower buffer tank 62 (shown in FIG. 7) and electrophoresis can be performed once both the upper and lower tanks are filled with an appropriate buffer solution and the two electrodes 60 are electrically connected. During electrophoresis, bubbles created by the positive anode in the lower buffer tank 62 rise to the vertex of the inverted V-shaped conduit 56 and are diverged to the two sides of the main body through the side holes 58. Upon completion, the loaded main body is removed from the lower buffer tank 62 and the processed gels are then detached from the clamping devices 28 for post-electrophoresis handling.

Figure 10:
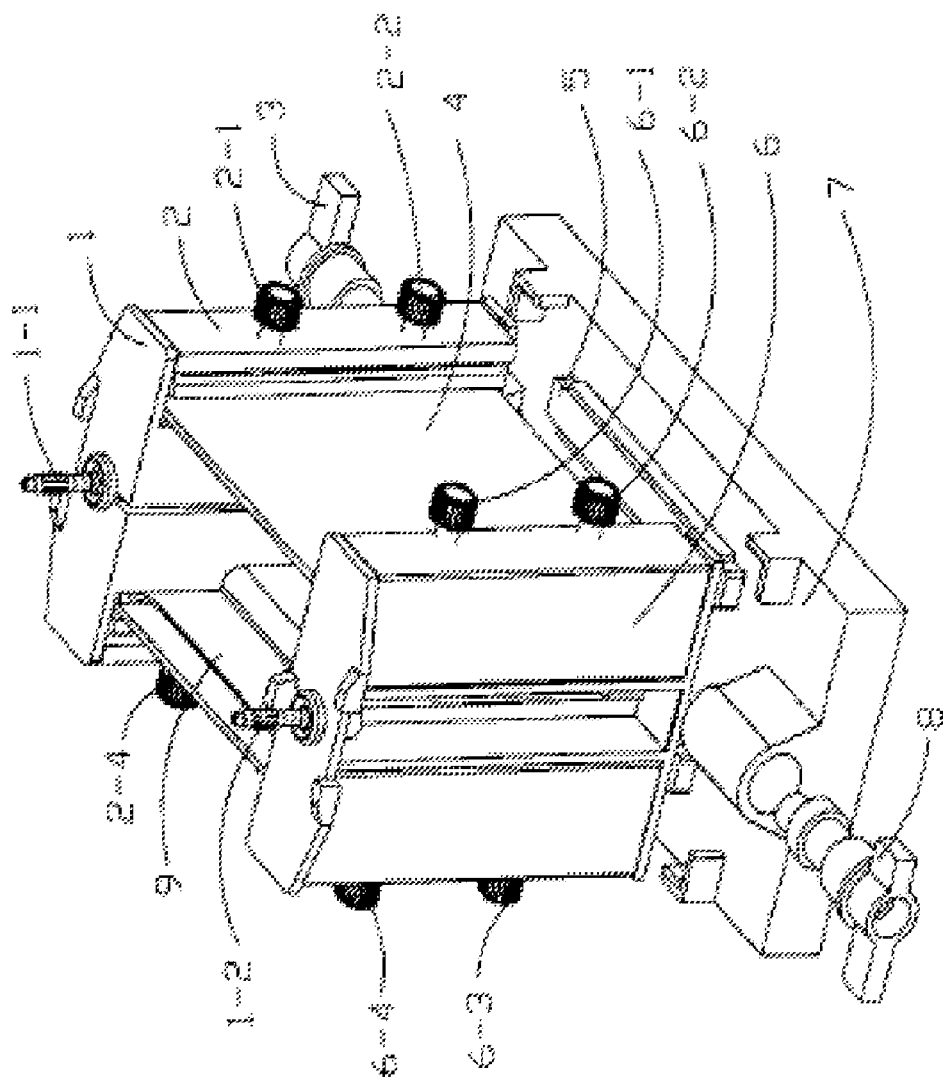
FIG. 10 is a perspective view of an apparatus for performing vertical electrophoresis comprising a main body attached on a casting base according to one embodiment of the present invention.
Figure 11:
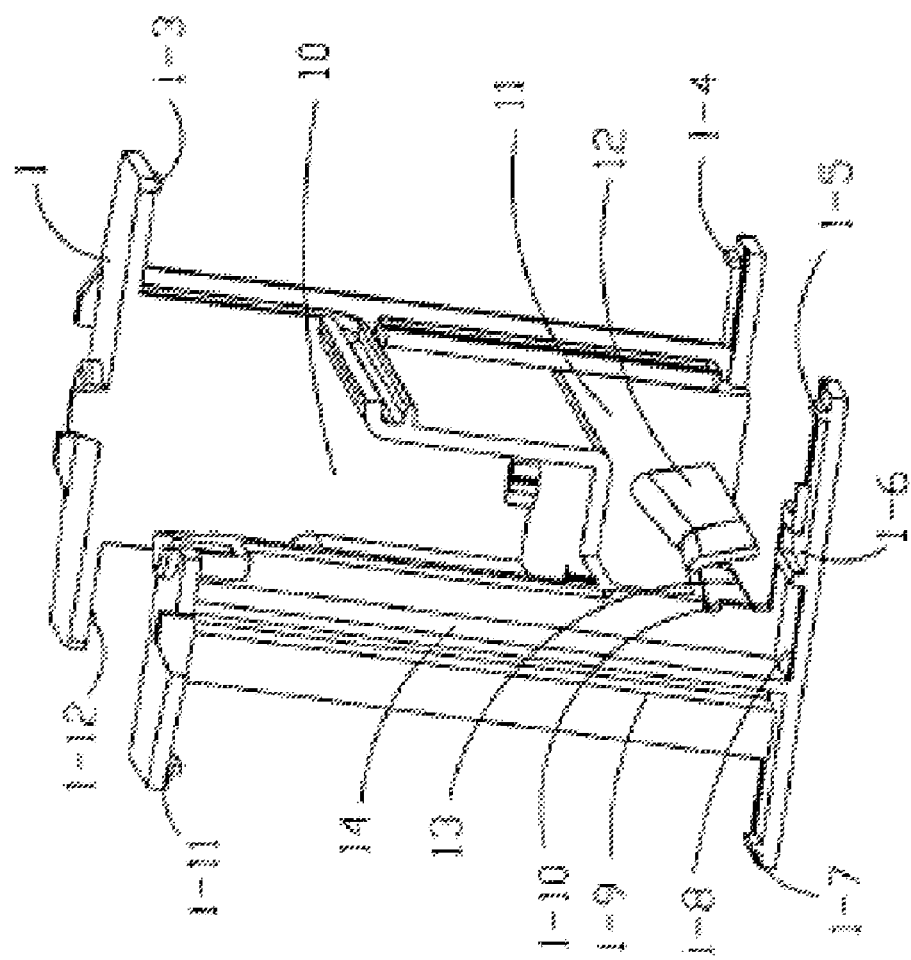
FIG. 11 is a side sectional view of a main body according to the same embodiment of the present invention.

The following description as illustrated in FIGS. 10 and 11 is of a specific preferred embodiment of the instant invention.

An apparatus for performing vertical electrophoresis as shown in FIG. 10 consists of an upper part and a lower part. The upper part consists of 2 pairs of clamping devices (2 & 6) affixed on the H-shaped main body 1 for clamping gel plates (4 & 9). The middle portion of the main body 1 is an upper buffer tank 10, and the lower portion of the main body is a lower buffer tank 11 (both tanks are shown in FIG. 11). The upper (1-1) and lower (1-2) buffer tank electrodes are provided on the main body 1. The clamping devices (2 & 6) are U-shaped with a bolstering panel affixed inside the U-shaped structure of each clamping device (2 & 6) by means of fixing screws (2-1, 2-2, 2-4, 6-1, 6-2, 6-3 & 6-4). The upper part is securely fixed on the casting base 7 with rod-shaped rubber sealing 5 deposited thereon and underneath the gel plates (4 & 9). The casting base 7 further contains rotary locking systems (3 & 8) provided on either side of the casting base 7 for affixing the main body 1 to the casting base 7 through the attachment of the rotary locking systems (3 & 8) onto the pressure board 1-8 (shown in FIG. 11) on the main body 1.

The detailed structure of the main body 1 is further illustrated in FIG. 11 in which the middle portion is the upper buffer tank 10 with the lower buffer tank 11 being deposited therebelow. The upper 10 and lower 11 buffer tanks are formed when the grooves deposited on the side clamps (2 & 6) connect to the corresponding rails (1-3, 1-4, 1-5, 1-7, 1-11 & 1-12) on the main body 1, coupled with the attachment of the inner portion of the gel plates (4 & 9) to the rubber gasket disposed on the sides of the upper buffer tank 10. The bottom sides of the gel plates (4 & 9) attach securely to rubber sealings 5 deposited on the casting base 7 (as shown in FIG. 10). A platinum wire 13 is deposited under the ridge of the inverted V-shaped conduit 12 in the lower buffer tank 11. Side holes 1-10 adapted for diverging air bubbles to the two sides are provided on top of the conjunctions between the main body 1 and the inverted V-shaped conduit 12. On the two sides of the main body 1, a channel 1-9 is provided thereon and adapted for securing the inner side of the U-shape of the clamping devices (2 & 6) into the channel 1-9. Further, a pressure board 1-8 strengthened by the reinforcement structure 14 is deposited horizontally on the bottom of each side of the main body 1.

The preferred embodiments of the present invention are thus fully described. Although the description referred to particular embodiments, it will be clear to one skilled in the art that the present invention may be practiced with variation of these specific details. Hence this invention should not be construed as limited to the embodiments set forth herein.

For example, the gel plates 30 are described as being inserted into the main body 26 by a lateral movement, but it is clear that it may also be slid into the main body 26 from the top by a vertical motion. The gel plates 30 may be made of glass, ceramic, or other materials that are strong enough to hold the gels securely in place. Although an additional pair of gel plates 66 is loaded to the main body 26 as illustrated in FIG. 8, it is clear that a single dummy plate may also be used to replace the additional gel plates should only one gel is cast and processed.

As described above, rails 52 are provided on the upper boards 48 and the lower boards 50 for mating with grooves 74 disposed within the ends of the first ledge 70 of the clamping devices 28. However, it is clear to one skilled in the art that the rails may be disposed on one of the ledges for coupling with a groove disposed within the upper boards and the lower boards to deliver similar sliding movements for the clamping devices.

The two U-shaped clamping devices on the same side of the main body may be connected together as a single clamping unit such that these inter-connected clamps can be operated or moved simultaneously by just one single action to increase the efficiency of the process of affixing the gel plates onto the main body. Although the outer abutment panel 38 is described a L-shaped vertical panel, it is clear to one skilled in the art that this abutment panel may be provided in other shapes as long as a channel can be created between the outer abutment panel and the corresponding inner abutment panel to receive the ledge of the clamping device to ensure proper horizontal movement during the process of sliding between the loading and locking positions.

The rubber gasket is to ensure a leak-proof attachment of the gel plates 30 to the main body 26. The U-shaped slot 64 is adapted to allow different rubber gaskets to be easily interchangeable for adapting to different types of gel plates 30. For instance, a rubber gasket of uniform thickness may be used for an inner plate with lugs, while a rubber gasket of non-uniform thickness with two thickened ends acts as a functional substitute for the missing lugs if an inner plate without lugs is used.

What is claimed is:

1. An apparatus for performing vertical gel electrophoresis comprising:
   a) a main body further comprising
      a pair of H-shaped frames with each said frame further comprising two side panels and a bridge therebetween; and
      a base panel adapted for adjoining said bridges of said H-shaped frames such that a space created therebetween forms a partial upper buffer tank, said base panel acts as the floor of said partial upper buffer tank;
   b) at least one pair of gel plates;
   c) at least one pair of clamping devices attachable to said main body for securing said pair of gel plates to said main body such that said pair of gel plates may be attached to said main body in a position to form an upper buffer tank, wherein
      each said clamping device is U-shaped and further comprises a first ledge, a second ledge connected to and facing said first ledge, and a bolstering panel coupled to the interior side of said first ledge with a fixing mechanism for fixedly mounting said gel plates to said main body; and
   d) a lower buffer tank adapted to connect with said main body and said gel plates such that a gel cast within said pair of gel plates acts to electrically connect said upper and lower buffer tanks during operation; wherein
   said clamping devices are slidably attached to the sides of said main body in a manner to allow horizontal sliding movement of said clamping devices between a loading position and a locking position; said clamping devices in said loading position allow said gel plates to be inserted into said main body; said clamping devices in said locking position allow for secure attachment of said gel plates to said main body;
   each said side panel further comprises at least one inner abutment panel and at least one outer abutment panel extending therefrom; said inner abutment panel is positioned with said outer abutment panel in a manner that a channel is formed therebetween; said channel is adapted to accommodate said second ledge of said clamping device into said locking position such that said clamping device may be conveniently slid between said loading and said locking positions;
   each said side panels further comprises at least one side hole; and
   said apparatus further comprises an inverted V-shaped open conduit extending horizontally across and below said base panel with each of the two ends of said conduit connecting to each said side panel above said side hole such that during operation, bubbles formed in said lower buffer tank are diverged along said conduit to the sides of said main body through said side holes.

2. The apparatus according to claim 1 wherein said gel plates are made of ceramic.

3. The apparatus according to claim 1 wherein said main body further comprises
   a) a pair of upper boards with each said upper board connecting to the top of each said side panel of said H-shaped frames; and
   b) a pair of lower boards with each said lower board connecting to the bottom of each said side panel of said H-shaped frames.

4. The apparatus according to claim 3 wherein
   a) each said clamping device further comprises at least a pair of grooves with each groove provided within each end of said first ledge; and
   b) each said upper and lower board further comprises at least one rail extending horizontally thereacross;
   each said rail protrudes towards the center of said main body for coupling with said groove of the corresponding clamping device to guide the horizontal sliding movement of said clamping device between said loading and locking positions.

5. The apparatus according to claim 3 wherein
   a) each said clamping device further comprises at least one rail each provided on each end of said first ledge and extending horizontally thereacross; and
   b) each said upper and lower board further comprises at least a pair of grooves provided therewithin;
   each said rail protrudes towards the center of said clamping device for coupling with said groove of the corresponding upper or lower board to guide the horizontal sliding movement of said clamping device between said loading and locking positions.

6. An apparatus for performing vertical gel electrophoresis comprising:
   a) a main body further comprising a pair of H-shaped frames with each said frame further comprising two side panels and a bridge therebetween wherein,
      each said H-shaped frame further comprises a gasket of uniform thickness, a gasket of non-uniform thickness, and a U-shaped slot disposed along said two side panels and said bridge, said slot is adapted to receive a rubber gasket therein; said rubber gasket is adapted to form a leak-proof seal between said inner plate and said H-shaped frame during operation;
   b) at least one pair of gel plates comprising an inner plate fixed and juxtaposing an outer plate with a gel space provided therebetween; and
   c) at least one pair of clamping devices attachable to said main body for securing said pair of gel plates to said main body such that said pair of gel plates may be attached to said main body in a position to form an upper buffer tank, wherein
      each said clamping device is U-shaped and further comprises a first ledge, a second ledge connected to and facing said first ledge, and a bolstering panel coupled to the interior side of said first ledge with a fixing mechanism for fixedly mounting said gel plates to said main body; and
   d) a lower buffer tank adapted to connect with said main body and said gel plates such that a gel cast within said pair of gel plates acts to electrically connect said upper and lower buffer tanks during operation; wherein
   said clamping devices are slidably attached to the sides of said main body in a manner to allow horizontal sliding movement of said clamping devices between a loading position and a locking position; said clamping devices in said loading position allow said gel plates to be inserted into said main body; said clamping devices in said locking position allow for secure attachment of said gel plates to said main body;

each said side panel further comprises at least one inner abutment panel and at least one outer abutment panel extending therefrom; said inner abutment panel is positioned with said outer abutment panel in a manner that a channel is formed therebetween; said channel is adapted to accommodate said second ledge of said clamping device into said locking position such that said clamping device may be conveniently slid between said loading and said locking positions; and said rubber gasket is interchangeable between said gasket of uniform thickness and said gasket of non-uniform thickness; said gasket of uniform thickness is adapted to form a leak-proof seal between a notched inner plate and said H-shaped frame, said notched inner plate comprises a pair of lugs projecting from a rectilinear plate; said gasket of non-uniform thickness with a pair of thickened ends is adapted to form a leak-proof seal between an inner plate without lugs and said H-shaped frame.

7. The apparatus according to claim 6 wherein said gel plates are made of ceramic.

8. The apparatus according to claim 6 wherein said main body further comprises
   a) a pair of upper boards with each said upper board connecting to the top of each said side panel of said H-shaped frames; and
   b) a pair of lower boards with each said lower board connecting to the bottom of each said side panel of said H-shaped frames.

9. The apparatus according to claim 8 wherein
   a) each said clamping device further comprises at least a pair of grooves with each groove provided within each end of said first ledge; and
   b) each said upper and lower board further comprises at least one rail extending horizontally thereacross;
   each said rail protrudes towards the center of said main body for coupling with said groove of the corresponding clamping device to guide the horizontal sliding movement of said clamping device between said loading and locking positions.

10. The apparatus according to claim 8 wherein
    a) each said clamping device further comprises at least one rail each provided on each end of said first ledge and extending horizontally thereacross; and
    b) each said upper and lower board further comprises at least a pair of grooves provided therewithin;
    each said rail protrudes towards the center of said clamping device for coupling with said groove of the corresponding upper or lower board to guide the horizontal sliding movement of said clamping device between said loading and locking positions.

11. An apparatus for performing gel electrophoresis comprising:
    a) a main body further comprising
       i) two H-shaped frames each comprising two vertical side panels and a bridge therebetween; each said side panel comprising a vertical and outwardly extending inner abutment panel and a vertical and outwardly extending outer abutment panel with a channel disposed therebetween; said bridge comprising a vertically disposed panel spanning horizontally between said side panels;
       ii) a pair of upper boards each horizontally attached to the top of said side panel of said H-shaped frame further comprising a rail provided on each end extending horizontally thereacross;
       iii) a pair of lower boards each horizontally attached to the bottom of said side panel of said H-shaped frame further comprising a rail provided on each end extending horizontally thereacross; and
       iv) a base panel horizontally adjoining said two bridges of said two H-shaped frames and acting as the floor of a partial upper buffer tank created in the space therebetween:
    b) at least one pair of gel plates each pair comprising an inner plate fixed and juxtaposing an outer plate with a gel space provided therebetween;
    c) two pairs of U-shaped clamping devices each comprising a first ledge connecting a second ledge, and a bolstering panel coupled to the interior side of said first ledge; said first ledge further comprising a groove provided within each end, said grooves adapted for mating with said rails of said upper board and said lower board when said clamping device is coupled to said main body; and
    d) a lower buffer tank adapted to receive said main body therein; wherein
    each side of said H-shaped frame forms a sliding joint for connection with said U-shaped clamping device such that said clamping device is slidable horizontally between a loading position and a locking position; said clamping device in said loading position allows said gel plates to be inserted into said main body; said clamping device in said locking position allows for abutment of said gel plates to said main body and tightening of said bolstering panel secures said gel plates into a position to form an upper buffer tank;
    said sliding movement of each said clamping device is guided by the traversing of said rail within said groove and the interpolating relationship between said second ledge and said channel;
    a gel cast within said gel space acts to electrically connect said lower and upper buffer tanks during operation; and
    each said side panel further comprises a side hole positioned below said base panel, said main body further comprises an inverted V-shaped open conduit extending horizontally across and below said base panel with each end connecting to each said side panel and above said side hole such that during operation, bubbles formed in said lower buffer tank are diverged along said inverted V-shaped open conduit to the sides of said main body through said side hole.

12. An apparatus for performing gel electrophoresis comprising:
    a) a main body further comprising
       i) two H-shaped frames each comprising two vertical side panels and a bridge therebetween; each said side panel comprising a vertical and outwardly extending inner abutment panel and a vertical and outwardly extending outer abutment panel with a channel disposed therebetween; said bridge comprising a vertically disposed panel spanning horizontally between said side panels;
       ii) a pair of upper boards each horizontally attached to the top of said side panel of said H-shaped frame further comprising a rail provided on each end extending horizontally thereacross;
       iii) a pair of lower boards each horizontally attached to the bottom of said side panel of said H-shaped frame further comprising a rail provided on each end extending horizontally thereacross; and iv) a base panel horizontally adioininq said two bridges of said two H-shaped frames and acting as the floor of a partial upper buffer tank created in the space therebetween;

b) at least one pair of gel plates each pair comprising an inner plate fixed and juxtaposing an outer plate with a gel space provided therebetween;

c) two pairs of U-shaped clamping devices each comprising a first ledge connecting a second ledge, and a bolstering panel coupled to the interior side of said first ledge; said first ledge further comprising a groove provided within each end, said grooves adapted for mating with said rails of said upper board and said lower board when said clamping device is coupled to said main body; and d) a lower buffer tank adapted to receive said main body therein; wherein each side of said H-shaped frame forms a sliding joint for connection with said U-shaped clamping device such that said clamping device is slidable horizontally between a loading position and a locking position; said clamping device in said loading position allows said gel plates to be inserted into said main body; said clamping device in said locking position allows for abutment of said gel plates to said main body and tightening of said bolstering panel secures said gel plates into a position to form an upper buffer tank;

said sliding movement of each said clamping device is guided by the traversing of said rail within said groove and the interpolating relationship between said second ledge and said channel;

a gel cast within said gel space acts to electrically connect said lower and upper buffer tanks during operation; and each said H-shaped frame further comprises a gasket of uniform thickness, a gasket of non-uniform thickness and a U-shaped slot disposed along said two side panels and said bridge, said slot is adapted to receive a rubber gasket therein; said rubber gasket is interchangeable between said gasket of uniform thickness and said gasket of non-uniform thickness to form a leak-proof seal between said inner plate and said H-shaped frame during operation, wherein e) said gasket of uniform thickness is adapted to form a leak-proof seal between a notched inner plate and said H-shaped frame, said notched inner plate comprises a pair of lugs projecting from a rectilinear plate; and f) said gasket of non-uniform thickness with a pair of thickened ends is adapted to form a leak-proof seal between an inner plate without lugs and said H-shaped frame.

13. An apparatus for performing gel electrophoresis comprising:

a) a main body further comprising i) two H-shaped frames each comprising two vertical side panels and a bridge therebetween; each said side panel comprising a vertical and outwardly extending inner abutment panel and a vertical and outwardly extending outer abutment panel with a channel disposed therebetween; said bridge comprising a vertically disposed panel spanning horizontally between said side panels;

ii) a pair of upper boards each horizontally attached to the top of said side panel of said H-shaped frame further comprising a pair of grooves provided therewithin;

iii) a pair of lower boards each horizontally attached to the bottom of said side panel of said H-shaped frame further comprising a pair of grooves provided therewithin; and iv) a base panel horizontally adjoining said two bridges of said two H-shaped frames and acting as the floor of a partial upper buffer tank created in the space therebetween;

b) at least one pair of gel plates each pair comprising an inner plate fixed and iuxtaposing an outer plate with a gel space provided therebetween;

c) two pairs of U-shaped clamping devices each comprising a first ledge connecting a second ledge, and a bolstering panel coupled to the interior side of said first ledge; said first ledge further comprising a rail provided on each end of said first ledge and extending horizontally thereacross, said rails adapted for mating with said grooves of said upper board and said lower board when said clamping device is coupled to said main body; and d) a lower buffer tank adapted to receive said main body therein; wherein each side of said H-shaped frame forms a sliding joint for connection with said U-shaped clamping device such that said clamping device is slidable horizontally between a loading position and a locking position; said clamping device in said loading position allows said gel plates to be inserted into said main body; said clamping device in said locking position allows for abutment of said gel plates to said main body and tightening of said bolstering panel secures said gel plates into a position to form an upper buffer tank;

said sliding movement of each said clamping device is guided by the traversing of said rail within said groove and the interpolating relationship between said second ledge and said channel;

a gel cast within said gel space acts to electrically connect said lower and upper buffer tanks during operation; and said each side panel further comprises a side hole positioned below said base panel, said main body further comprises an inverted V-shaped open conduit extending horizontally across and below said base panel with each end connecting to each said side panel and above said side hole such that during operation, bubbles formed in said lower buffer tank are diverged along said inverted V-shaped open conduit to the sides of said main body through said side hole.

14. An apparatus for performing gel electrophoresis comprising:

a) a main body further comprising i) two H-shaped frames each comprising two vertical side panels and a bridge therebetween; each said side panel comprising a vertical and outwardly extending inner abutment panel and a vertical and outwardly extending outer abutment panel with a channel disposed therebetween; said bridge comprising a vertically disposed panel spanning horizontally between said side panels;

ii) a pair of upper boards each horizontally attached to the top of said side panel of said H-shaped frame further comprising a pair of grooves provided therewithin;

iii a pair of lower boards each horizontally attached to the bottom of said side panel of said H-shaped frame further comprising a pair of grooves provided therewithin; and iv) a base panel horizontally adjoining said two bridges of said two H-shaped frames and acting as the floor of a partial upper buffer tank created in the space therebetween;

b) at least one pair of gel plates each pair comprising an inner plate fixed and iuxtaposing an outer plate with a gel space provided therebetween;

c) two pairs of U-shaped clamping devices each comprising a first ledge connecting a second ledge, and a bolstering panel coupled to the interior side of said first ledge; said first ledge further comprising a rail provided on each end of said first ledge and extending horizontally thereacross, said rails adapted for mating with said grooves of said upper board and said lower board when said clamping device is coupled to said main body; and d) a lower buffer tank adapted to receive said main body therein; wherein each side of said H-shaped frame forms a sliding joint for connection with said U-shaped clamping device such that said clamping device is slidable horizontally between a loading position and a locking position; said clamping device in said loading position allows said gel plates to be inserted into said main body; said clamping device in said locking position allows for abutment of said gel plates to said main body and tightening of said bolstering panel secures said gel plates into a position to form an upper buffer tank;

said sliding movement of each said clamping device is guided by the traversing of said rail within said groove and the interpolating relationship between said second ledge and said channel;

a gel cast within said gel space acts to electrically connect said lower and upper buffer tanks during operation; and each said H-shaped frame further comprises a gasket of uniform thickness, a gasket of non-uniform thickness and a U-shaped slot disposed along said two side panels and said bridge, said slot is adapted to receive a rubber gasket therein; said rubber gasket is interchangeable between said gasket of uniform thickness and said gasket of non-uniform thickness to form a leak-proof seal between said inner plate and said H-shaped frame during operation, wherein e) said gasket of uniform thickness is adapted to form a leak-proof seal between a notched inner plate and said H-shaped frame, said notched inner plate comprises a pair of lugs projecting from a rectilinear plate; and f) said gasket of non-uniform thickness with a pair of thickened ends is adapted to form a leak-proof seal between an inner plate without lugs and said H-shaped frame.

* * * * *